(12) United States Patent
Bodjanski (10) Patent No.: US 10,219,866 B2
(45) Date of Patent: Mar. 5, 2019

(54) OPTICAL TRACKING METHOD AND SYSTEM BASED ON PASSIVE MARKERS

(71) Applicant: OptiNav Sp. Z o.o., Slupsk (PL)

(72) Inventor: Mariusz Bodjanski, Zielonka (PL)

(73) Assignee: OPTINAV SP. Z O.O., Slupsk (PL)

( * ) Notice: Subject to any disclaimer, the term of this patent is extended or adjusted under 35 U.S.C. 154(b) by 142 days.

(21) Appl. No.: 15/497,826

(22) Filed: Apr. 26, 2017

(65) Prior Publication Data

US 2017/0258531 A1   Sep. 14, 2017

Related U.S. Application Data

(63) Continuation of application No. PCT/EP2015/075270, filed on Oct. 30, 2015.

(30) Foreign Application Priority Data

Nov. 3, 2014  (EP) .................................... 14461587

(51) Int. Cl.
*A61B 90/00* (2016.01)
*G06T 7/00* (2017.01)
(Continued)

(52) U.S. Cl.
CPC .............. *A61B 34/20* (2016.02); *A61B 90/39* (2016.02); *A61B 90/92* (2016.02); *G06T 7/13* (2017.01);
(Continued)

(58) Field of Classification Search
CPC ................................. A61B 90/00; G06T 7/00
(Continued)

(56) References Cited

U.S. PATENT DOCUMENTS 6,351,659 B1   2/2002  Vilsmeier
6,877,239 B2   4/2005  Leitner et al.
(Continued)

FOREIGN PATENT DOCUMENTS

DE   10 2006 060 716 A1   6/2008
WO   2004/002352 A2   1/2004

OTHER PUBLICATIONS

International Search Report for PCT/EP2015/075270; dated Jan. 26, 2016; 14 pp.
(Continued)

*Primary Examiner* — Abolfazl Tabatabai
(74) *Attorney, Agent, or Firm* — Harness, Dickey & Pierce, P.L.C.

(57) ABSTRACT

An elliptical, optical-tracking marker comprises an inner marker body that is filled with radially spread color spectrum points with respect to a center point of the inner marker body. A color value of each spectrum point of the inner marker body is calculated as a function of an angle defined between a horizontal line crossing the central point of the inner marker body and a line crossing the central point of the inner marker as well as the given pixel in such a manner, that the color values of the respective spectrum points vary in accordance with a sinusoidal pattern along an elliptical path around the center point, in particular along a circular path centered around the center point. A method and a system for determining a 3D position of an object in space use the characteristics of this marker by detecting and analyzing the sinusoidal pattern.

28 Claims, 4 Drawing Sheets

(51) Int. Cl.
   *A61B 34/20* (2016.01)
   *A61B 90/92* (2016.01)
   *G06T 7/13* (2017.01)
   *G06T 7/90* (2017.01)
   *G06T 7/70* (2017.01)
   *H04N 7/18* (2006.01)

(52) U.S. Cl.
   CPC .................. *G06T 7/70* (2017.01); *G06T 7/90* (2017.01); *H04N 7/181* (2013.01); *A61B 2034/2055* (2016.02); *A61B 2034/2057* (2016.02); *A61B 2034/2065* (2016.02); *A61B 2090/3937* (2016.02); *A61B 2090/3983* (2016.02); *G06T 2207/10016* (2013.01); *G06T 2207/30204* (2013.01)

(58) Field of Classification Search
   USPC .......................................... 382/103; 348/169
   See application file for complete search history.

(56) References Cited

U.S. PATENT DOCUMENTS

| | | | |
|---|---|---|---|
| 7,780,681 B2 * | 8/2010 | Sarin ..................... | A61B 5/103 606/102 |
| 8,502,991 B2 | 8/2013 | Daxauer et al. | |
| 2011/0254922 A1 | 10/2011 | Schaerer et al. | |
| 2012/0307021 A1 | 12/2012 | Tsai et al. | |

OTHER PUBLICATIONS

Qingyi Gu et al.; Fast Tracking System for Multi-colored Pie-shaped Markers; 2012; 6 pp.

* cited by examiner

OPTICAL TRACKING METHOD AND SYSTEM BASED ON PASSIVE MARKERS

CROSS-REFERENCE TO RELATED APPLICATIONS

This application is a continuation of international patent application PCT/EP2015/075270 filed on Oct. 30, 2015 designating the U.S., which international patent application claims priority from European patent application 14461587.9 filed on Nov. 3, 2014. The entire contents of these priority applications are incorporated herein by reference.

BACKGROUND OF THE INVENTION

The present invention relates to optical tracking systems and methods based on passive markers. In particular the present invention relates to improvements in passive markers themselves and to improvements in accuracy of passive marker based methods and systems.

Prior art optical systems utilize data captured from image sensors to determine the 3D position of an object imaged by one or more cameras calibrated to provide overlapping projections. Data acquisition is traditionally implemented using special markers attached to the object or adhering to the object. These systems produce data with 3 degrees of freedom for each marker, and rotational information must typically be inferred from the relative orientation of three or more markers. Some prior art systems are disclosed, for instance, by US 2011/0254922 A1 or WO 2004/002352 A2.

Known passive optical systems use markers coated with a retroreflective material to reflect light that is generated near the camera lens. The threshold of the camera can be adjusted so that only the bright reflective areas will be sampled.

Typically, the known markers have a checkered bright-and-dark pattern. The centroid of the marker is typically defined by an intersection of straight edges formed between alternating bright and dark regions. The centroid is estimated as a position of the marker within the two-dimensional image that is captured.

An object with markers attached at known positions is used to calibrate the cameras and obtain their positions and the lens distortion of each camera is measured. If two calibrated cameras see a marker, a three-dimensional fix can be obtained (source: Wikipedia).

There are however optical tracking applications requiring a high degree of accuracy, such as medial applications, high-precision mechanical applications, precise constructional components measurements. For example replacement surgery success heavily depends on proper positioning of replacement implants.

Computer assisted surgery (CAS—source: Wikipedia) represents a surgical concept and set of methods, that use computer technology for presurgical planning, and for guiding or performing surgical interventions. CAS is also known as computer aided surgery, computer assisted intervention, image guided surgery and surgical navigation, but these terms are more or less synonyms with CAS. CAS has been a leading factor for the development of robotic surgery. In CAS, computerized models are used to ensure correct objects (such as bones) alignment. Tracking of surgical instruments and components in relation to patient anatomy is also of great importance.

It would be advantageous to improve accuracy of measurement while applying cost-effective passive markers.

U.S. Pat. No. 6,877,239 B2, entitled "Method and device for checking a marking element for displacement" ("'239 patent") discloses a method for checking a marking element for displacement in relation to a holding structure, in particular a bone, on which this marking element is fixed, said marking element being used for determining position in navigational surgery, and said marking element functioning with the greatest possible precision, it is proposed to choose a point of orientation which is in a unique relationship to the holding structure and to monitor the position of the point of orientation in a reference system of the marking element.

According to '239 patent, the position of a marking element in space can be determined via a navigation station. For example, a marking element for this purpose comprises a large number of transmitters such as ultrasound transmitters or infrared transmitters whose signals can be registered by receivers. In particular, three receivers are provided for the three spatial coordinates.

A drawback of the '239 patent is that active markers are used such as ultrasound transmitters or infrared transmitters. This makes the system more expensive and the marker devices require more space in the operating area than passive markers.

Another publication of U.S. Pat. No. 7,780,681 B2, entitled "Non-imaging, computer assisted navigation system for hip replacement surgery" ("'681 patent"), discloses a locating system; a computer, interfaced to the locating system and interpreting the positions of tracked objects in a generic computer model of a patient's hip geometry; a software module, executable on the computer, which defines the patient's pelvic plane without reference to previously obtained radiological data, by locating at least three pelvic landmarks; and a pelvic tracking marker, fixable to the pelvic bone and trackable by the locating system, to track in real time the orientation of the defined pelvic plane. Preferably, the system also includes a femoral tracking marker, securely attachable to a femur of the patient by a non-penetrating ligature and trackable by the locating system to detect changes in leg length and femoral offset.

U.S. Pat. No. 6,351,659 B1, entitled "Neuro-navigation system" ("'659 patent") discloses a Neuro-navigation system comprising a reflector referencing system including passive reflectors and a marker system with markers or landmarks wherein the reflectors as well as the markers as regards their shape, size and material selection as well as their arrangement or attachment on the parts of the body to be operatively treated and on the surgical instruments are configured so that mapping their locations is substantially facilitated or is able to take place more accurately positioned by a computer/camera unit having a graphic display terminal as well as the operative treatment with the aid of this unit.

The '659 patent publication also discloses a referencing system for surgical instruments and operative treatment apparatus, said system comprising: a source of infrared radiation; plural cameras for detecting reflected infrared radiation; a computer connected to the cameras; plural adaptors each configured for removable attachment to a respective surgical instrument or operative treatment apparatus, and plural sets of at least three infrared reflectors secured to said plural adaptors. The plural sets of at least three infrared radiation reflectors include at least one spherical reflector.

The '681 and '659 patent publications disclose application of suitable optical markers utilizing multiple reflective spheres. Such passive reflective markers reflect infrared light emitted by suitable infrared illuminators.

Drawbacks of currently used reflective spheres include a need for replacement after single use or even during lengthy surgeries. Further, the reflective spheres are difficult to clean intra-operatively.

Afore-mentioned US 2011/0254922 A1 and DE 10 2006 060 716 A1 each disclose optical markers having an inner marker area providing intersecting edges, and having an outer marker area surrounding the inner marker area. The outer marker area may have an individual bright-and-dark pattern that serves as an identifier. While these passive marker systems avoid the disadvantages of active marker systems, it would be desirable to improve these known systems in order to obtain higher accuracy in a cost-efficient manner.

SUMMARY OF THE INVENTION

Accordingly, it is an object of the present invention to provide an improved passive marker based optical tracking method and system allowing for improved accuracy in a cost effective manner.

According to a first aspect of the invention, there is provided a method of determining a 3D position of an object in space, the method comprising the steps of attaching an optical-tracking marker to the object, said optical-tracking marker comprising an inner marker body having an elliptical shape and a geometric center, said inner marker body being filled with color spectrum points radially spread with respect to the geometric center, wherein a color value of each spectrum point of the inner marker body is calculated as a function of an angle defined between a horizontal line crossing the central point and a further line crossing the central point as well as the respective spectrum point, capturing a first digital image of said optical-tracking marker using a first camera and capturing a further digital image of said optical-tracking marker using a further camera, detecting, within the first and further digital images, edges of the optical-tracking marker, detecting blobs (or BLOBs) within a respective set of detected edges in the first and further digital images, detecting ellipses within a respective set of detected blobs, analyzing a sinusoidal pattern within each of the detected ellipses, determining, based on the analysis, a 2D location of the optical-tracking marker in each of the first digital image and the further digital image, and determining a 3D location of the optical-tracking marker in space based on the 2D locations in each of the first digital image and the further digital image.

According to a second aspect, there is provided a method of determining a 3D position of an object in space, the method comprising the steps of attaching at least two optical-tracking markers on the object, said at least two optical-tracking markers each comprising an inner marker body having an elliptical shape and a geometric center, said inner marker body being filled with color spectrum points radially spread with respect to the geometric center, wherein a color value of each spectrum point of the inner marker body is calculated as a function of an angle defined between a horizontal line crossing the central point and a further line crossing the central point as well as the respective spectrum point, capturing a digital image of said at least two optical-tracking markers using at least one camera, detecting, within the digital image, edges of the at least two optical-tracking markers, detecting blobs within a respective set of detected edges, detecting ellipses within a respective set of detected blobs, analyzing a sinusoidal pattern within each of the detected ellipses, determining, based on the analysis, 2D locations of the at least two optical-tracking markers, and determining a 3D position of the object in space based on the 2D locations.

According to yet another object, there is provided a system for determining a 3D position of an object in space, comprising at least one optical-tracking marker configured to be attached to the object, said optical-tracking marker comprising an inner marker body having an elliptical shape and a geometric center, said inner marker body being filled with color spectrum points radially spread with respect to the geometric center, wherein a color value of each spectrum point of the inner marker body is calculated as a function of an angle defined between a horizontal line crossing the central point and a further line crossing the central point as well as the respective spectrum point, at least one camera for capturing at least one digital image of said optical-tracking marker, and a processing unit configured to execute the steps of one at least one of the afore-mentioned methods.

Preferably, the step of analyzing the sinusoidal pattern includes a step of checking if a detected sinusoidal pattern matches a predefined expectation derived from known characteristics of the at least one marker.

According to yet another object, there is also provided an optical-tracking marker for determining a 3D position of an object in space, the marker comprising an inner marker body having an elliptical shape and a geometric center, said inner marker body being filled with color spectrum points radially spread with respect to the geometric center, wherein a color value of each spectrum point of the inner marker body is calculated as a function of an angle defined between a horizontal line crossing the central point and a further line crossing the central point as well as the respective spectrum point, wherein the color values of the respective spectrum points vary in accordance with a sinusoidal pattern along an elliptical path around the center point, in particular along a circular path centered around the center point.

According to yet another aspect, there is provided a computer program comprising program code for performing all the steps of the at least one of the aforementioned methods when said program is run on a computer. The computer program may be stored on a non-transitory, tangible computer readable medium.

BRIEF DESCRIPTION OF THE DRAWINGS

Further details and features of the present invention, its nature and various advantages will become more apparent from the following detailed description of preferred embodiments shown in a drawing, in which.

NOTATION AND NOMENCLATURE

Some portions of the detailed description which follows are presented in terms of data processing procedures, steps or other symbolic representations of operations on data bits that can be performed on computer memory. Therefore, a computer executes such logical steps thus requiring physical manipulations of physical quantities.

Usually these quantities take the form of electrical or magnetic signals capable of being stored, transferred, combined, compared, and otherwise manipulated in a computer system. For reasons of common usage, these signals are referred to as bits, packets, messages, values, elements, symbols, characters, terms, numbers, or the like.

Additionally, all of these and similar terms are to be associated with the appropriate physical quantities and are merely convenient labels applied to these quantities. Terms such as "processing" or "creating" or "transferring" or "executing" or "determining" or "detecting" or "obtaining" or "selecting" or "calculating" or "generating" or the like, refer to the action and processes of a computer system that manipulates and transforms data represented as physical (electronic) quantities within the computer's registers and memories into other data similarly represented as physical quantities within the memories or registers or other such information storage.

A computer-readable (storage) medium, such as referred to herein, typically may be non-transitory and/or comprise a non-transitory device. In this context, a non-transitory storage medium may include a device that may be tangible, meaning that the device has a concrete physical form, although the device may change its physical state. Thus, for example, non-transitory refers to a device remaining tangible despite a change in state.

DESCRIPTION OF PREFERRED EMBODIMENTS

Figure 1:
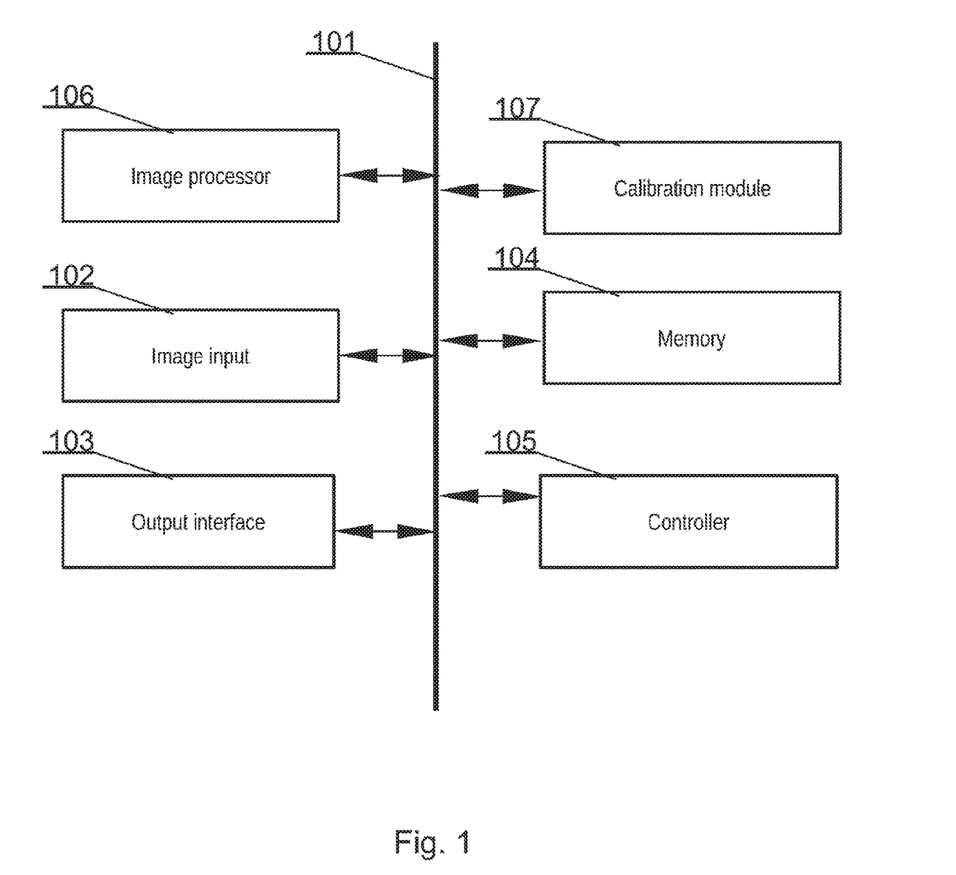
FIG. 1 presents a diagram of a system according to an embodiment of the present invention.

FIG. 1 presents a diagram of the system according to an embodiment of the present invention. The system comprises at least one passive marker, at least one camera (positioned such that the at least one passive marker is within its field of view) and a processing unit. In an advantageous embodiment of the present invention there are three cameras, located for example on an imaginary circle and spaced by a 120 degrees angle. Nevertheless, two or more than three cameras may be used depending on system data processing capability and communication interface(s) data throughput.

Parameters of cameras that are relevant for markers detection are resolution, sensitivity, photo-sensitive sensor size, focal length of a lens, a number of captured frames per second.

Preferably an output monitor is connected to the processing system for presentation of the optical tracking results. The cameras as well as the monitor will typically be mounted in a suitable stand.

The system may be realized using dedicated components or custom made FPGA or ASIC circuits. The system comprises a data bus 101 two-way-communicatively coupled to a memory 104. Additionally, other components of the system are communicatively coupled to the system bus 101 so that they may be managed by a controller 105.

The memory 104 may store one or more computer program or programs executed by the controller 105 in order to execute steps of the methods according to the present invention.

The system further comprises an input interface providing image input 102, the image being captured by the camera. Advantageously, stereo images will be provided as a left-right camera image pair. The images may be stored in the memory 104 for processing.

The processed data and results may be output via an output interface 103 such as an audio/video signal output interface eg. HDMI.

The system also incorporates a calibration module 107 configured to process configuration data and store system configuration data for future reference.

The calibration may be executed as follows. First there has to be executed internal calibration i.e. each camera is calibrated in order to determine the following parameters: fx, fy (focal length in pixels—pixel's dimensions may be different vertically and horizontally), cx, cy (coordinates of a sensor point, via which an optical axis of camera-lens passes—in pixels), k (radial distortion coefficients), p (tangent distortions coefficients). Such calibration may be effected by different methods, for example an analysis of a checkerboard photos shot at different angles.

As a second calibration step, external calibration is executed in order to determine geometry of the measuring system. This step is preferably executed on each change in the setup of the measuring system and comprises placing a reference pattern in a field of view of all cameras (it may be a set of markers (having known identifiers and dimensions) in a given spatial configuration). This process may be fully automatic.

Figure 2:
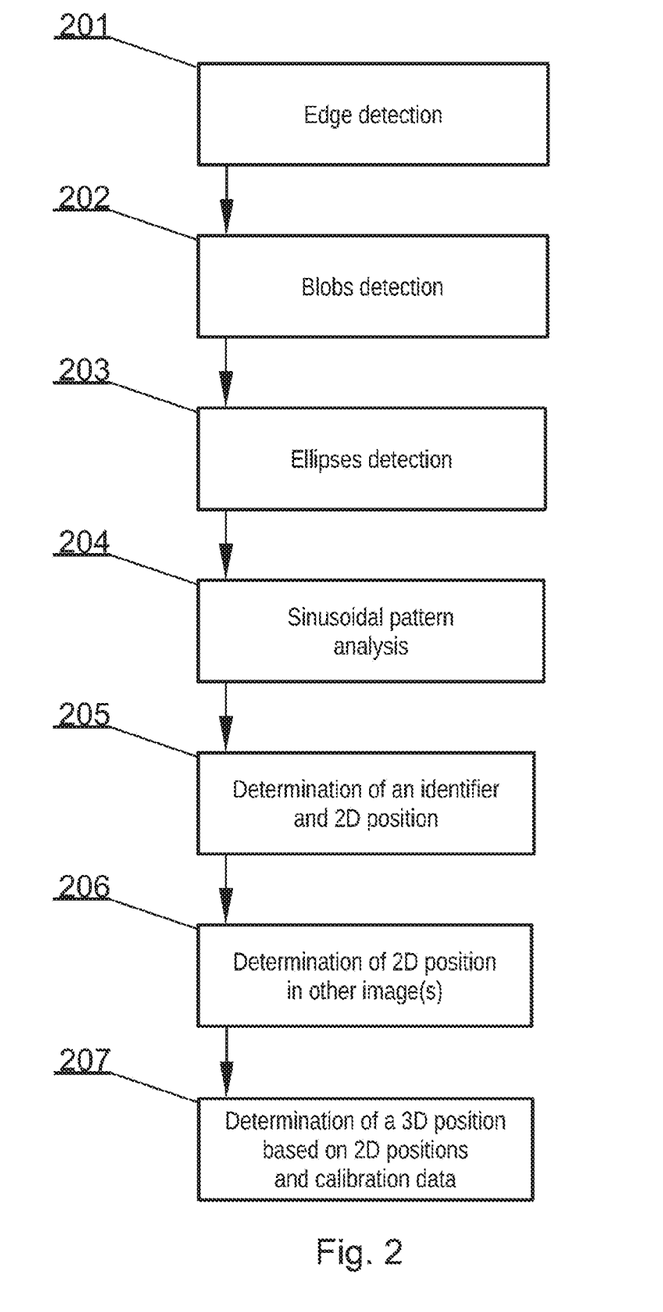
FIG. 2 presents a diagram for explaining a method according to an embodiment of the present invention.
Figure 3A:
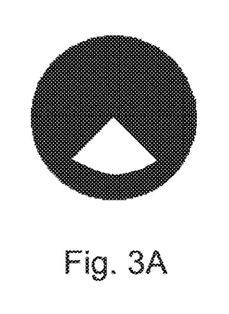
FIGS. 3A-3D present examples of passive markers according to embodiments of the present invention.
Figure 3B:
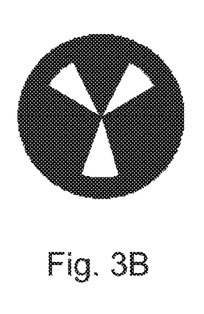
Figure 3C:
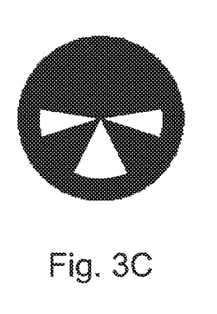
Figure 3D:
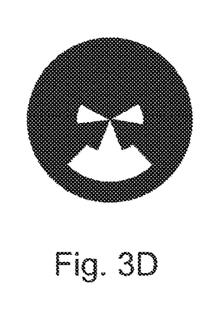

FIG. 2 presents a diagram of a method according to an embodiment of the present invention. The method starts at step 201 from marker's edge detection, within the digital image, followed by detection of blobs 202 within a set of detected edges. In the field of computer vision, blob (or BLOB for "Binary Large Object") detection refers to mathematical methods that are aimed at detecting regions in a digital image that differ in properties, such as brightness or color, compared to areas surrounding those regions. Informally, a blob (or BLOB) is a region of a digital image in which some properties are constant or vary within a prescribed range of values; all the points in a blob can be considered in some sense to be similar to each other.

Subsequently, at step 203, there are detected ellipses (or circles) within a set of identified blobs. Next, at step 204, there is analyzed a sinusoidal pattern within each of the ellipses (or circles). Based on the foregoing analysis there is determined an identifier and 2D location 205 of a marker. The identifier of a marker may be automatically determined by analyzing marker's image and identifying marker's parameters present in equation(s) defining the marker i.e. $C, A_1, f_1, \varphi_1, A_2, f_2, \varphi_2$ as defined in the remainder of this specification.

Subsequently, at step 206, there is executed determination of 2D position of the same marker in other image(s) obtained by other camera(s). When at least one 2D location of a marker is determined, the 3D position of this marker may be determined at step 207.

Two scenarios are be possible: 1) When a position of a tool, comprising at least one marker, is determined (2D location) by at least two cameras, its 3D position in space may be determined at step 207; 2) When a position of a tool, comprising of at least two markers, is determined (2D location) by at least one camera, its 3D position in space may be determined at step 207.

FIGS. 3A-3D present examples of passive markers according to the present invention. Each marker has an inner marker body that is filled with radially spread color spectrum points with respect to a geometric center of the inner marker body. The inner marker body may have elliptical shape which as such, is a generalization of a circle, which is a special type of an ellipse that has both focal points at the same location.

The color value of each point of the inner marker body is calculated as a function of an angle defined between a horizontal line crossing the central point of the inner marker body and a line crossing the central point of the inner marker as well as the given pixel. In other words, the color value of each point is dependent on its angular position, which may be expressed in polar coordinates of a polar coordinate system that is centered at the center point of the marker. In some embodiments, the color values of the spectrum points having the same angular position, i.e. being located on the same radial line, are the same.

Optionally, the inner marker body that is filled with radially spread color spectrum points with respect to a geometric center of the inner marker body may be such that a radius may be divided into at least two and preferably not more than 5 sections wherein different color generating functions apply to different sections. An advantage of such a marker will be greater information capacity thereby allowing a use of more markers in a given monitored area, such as an operating room.

In preferred embodiments of the present invention, the color value of each marker point is calculated according to the following equation:

$$R = C_R + A_{R1}\sin(f_{R1}\cdot\theta + \varphi_{R1}) + A_{R2}\sin(f_{R2}\cdot\theta + \varphi_{R2}) + \ldots + A_{RN}\sin(f_{RN}\cdot\theta + \varphi_{RN})$$

$$G = C_G + A_{G1}\sin(f_{G1}\cdot\theta + \varphi_{G1}) + A_{G2}\sin(f_{G2}\cdot\theta + \varphi_{G2}) + \ldots + A_{GN}\sin(f_{GN}\cdot\theta + \varphi_{GN})$$

$$B = C_B + A_{B1}\sin(f_{B1}\cdot\theta + \varphi_{B1}) + A_{B2}\sin(f_{B2}\cdot\theta + \varphi_{B2}) + \ldots + A_{BN}\sin(f_{BN}\cdot\theta + \varphi_{BN})$$

wherein

R, G, B—are color components;

C—is a fixed coefficient defining an average value of R, G, B;

A—is a value of amplitude of a geometric function such as a sine;

f—is a number of oscillations within a round angle unit or a frequency assuming values 1, 2, 3 . . . N being a number of sinusoidal components, with $N \leq 10$ and preferably $N \leq 5$ and even more preferred $N \leq 3$;

θ—is an angle defined between a horizontal line crossing the central point of the inner marker body and a line crossing the central point of the inner marker as well as the given pixel;

φ—is an initial phase—a parameter of a sine function for θ=0;

R,G,B—indexes of referenced color components.

The markers shown in FIGS. 3A-3D are gray-scale markers, wherein R=G=B and wherein $R = y = C + A_1\sin(f_1\Theta + \varphi_1) + A_2\sin(f_2\Theta + \varphi_2)$. Accordingly, the points of the markers of preferred embodiments have color values that vary in accordance with a sinusoidal pattern along an elliptical and preferably along a circular path around the center point of the respective marker, wherein the sinusoidal pattern includes one or two sinusoidal components having different frequencies, different phases and/or different amplitudes.

In some exemplary embodiments, the sinusoidal pattern may represent an individual identifier for the respective marker. Preferably, the sinusoidal pattern also serves as a basis for determining the 2D position of the marker in the captured image. Therefore, the sinusoidal pattern of each marker may by analyzed both for identifying an individual marker among a group of markers having different sinusoidal patterns, and for determining the 2D position of the respective marker in the captured image.

Some embodiments of the new method and system may employ a step of determining the 2D position of the marker in the captured image from the center point of the ellipse or circle detected by analysis of the sinusoidal pattern. Alternatively or additionally, a plurality of expectations (for example in the form of expected marker images or parameters of such expected marker images) may be derived from the known characteristics of the marker and may be stored in the memory of the computer, and the 2D position of the marker may be determined by comparing the captured image and the expectations.

An example of marker's parameters in accordance with one exemplary embodiment may be as follows:

$f_1 = 3$
$f_2 = 5$
$C = 0.25$
$A_1 = 0.25$
$A_2 = 0.25$
$\varphi_1 = 0$
$\varphi_2 = 0$ $$R = G = B = C + A_1*\cos(f_1*\theta + \varphi_1) + A_2*\cos(f_2*\theta + \varphi_2)$$

In case of a marker having its radius divided into sections, an example of marker's parameters may be as follows:

For radius Rn [0,0.5):
$f_1 = 3$;
$f_2 = 5$;
$C = 0.5$;
$A_1 = 0.25$;
$A_2 = 0.25$;
$\varphi_1 = 0$;
$\varphi_2 = pi/2$;

For radius Rn [0.5,1]:
$f_1 = 3$;
$f_2 = 5$;
$C = 0.5$;
$A_1 = 0.5$;
$A_2 = 0.5$;
$\varphi_1 = 0$;
$\varphi_2 = 0$;

$$R = G = B = C + A_1*\cos(f_1*\theta + \varphi_1) + A_2*\cos(f_2*\theta + \varphi_2)$$

According to embodiments of the present invention, the RGB color space may be changed to HSL/HSV, CMYK etc., i.e. to any other suitable color space.

Figure 4:
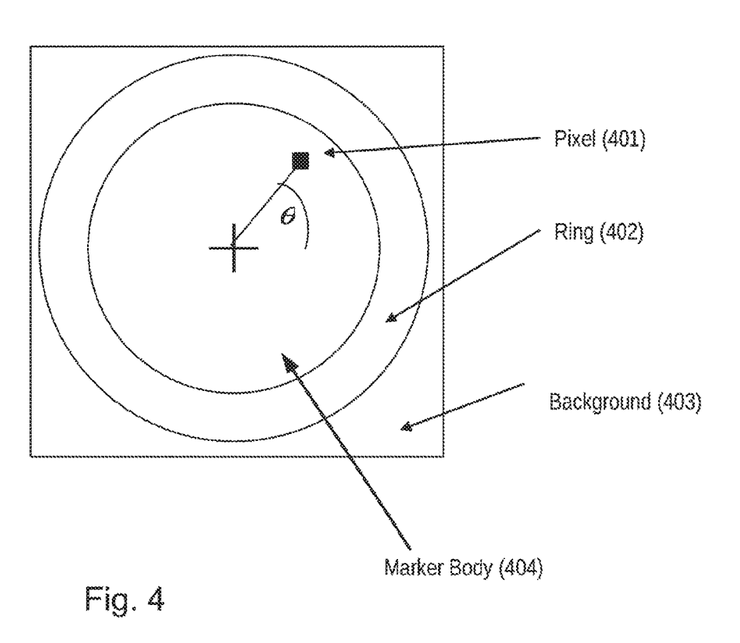
FIG. 4 shows a general embodiment of a passive marker according to embodiments of the present invention in a simplified form.

FIG. 4 shows a general embodiment of a passive marker in accordance with embodiments of the present invention. There is depicted a multi-part marker comprising a marker body 404 according to FIGS. 3A-3C. Additionally, the passive marker preferably comprises an outer ring 402 that may have a width equal to ¼ of a radius of the inner marker's body (However, other proportions are possible) 404. For example, the inner marker's body radius may have 16 mm while the ring is 4 mm.

Further, the marker may comprise a background 403, preferably of a uniform color.

The outer ring 402 allows for easy detection of marker's peripheral edge while the background 403 is a contrasting area around the outer ring 402 allowing to easily detect the outer ring. The outer ring may have different sizes with respect to the size of the marker. Both background and the outer ring may have different colors.

It is also to be noted that in case of RGB color space R=G=B which results in a gray-scale marker. In other advantageous embodiments, the marker is a grey-scale marker having a sinusoidal pattern with one, two or more (preferably not more than three) sinusoidal components, wherein the sinusoidal pattern is created merely from monochrome spectrum points having varying intensity values in accordance with the sinusoidal pattern. In yet further embodiments, the marker is a grey-scale marker having a sinusoidal pattern created by varying densities of black and white points.

An advantage of the markers according to the present invention is that they are identifiable at great angles with respect to the camera, such as up to 150°.

Further, there are many different marker configurations and thereby separate markers are easily identified as different markers in a scanned scene.

Additionally, the markers according to the present inventions may be relatively small with respect to the scanned scene.

The system according to the present invention has numerous advantages: a real view of a surgery table (due to application of human eye vision cameras instead of infrared), high resistance to pollutants or obstacles (such as blood etc), longer lifespan in surgical environment, low cost of a set of markers.

With application of Hamamatsu cameras, at a distance of about 4.7 m the results were std(z)=0.35 mm and excellent std(z)=0.02 mm at a distance of about 1.6 m for a single passive marker according to an embodiment of the present invention. In case of a plurality of markers the accuracy of measurement was much better.

Figure 5A:
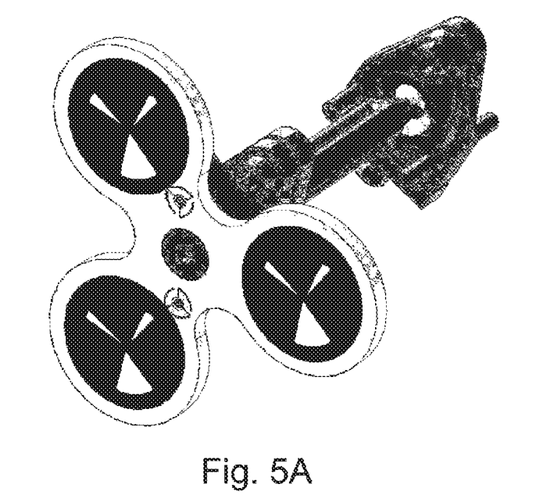
FIGS. 5A-5B present examples of devices having thereon passive markers according to embodiments of the present invention.
Figure 5B:
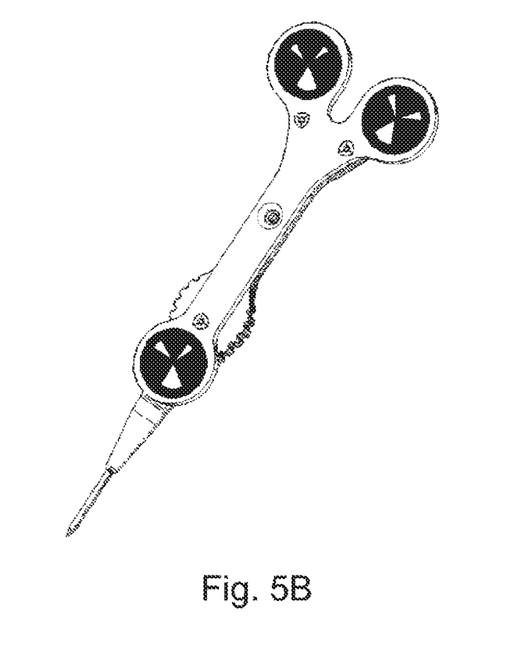

FIG. 5 presents examples of devices having thereon passive markers according to embodiments of the present invention. Three markers have been used in order to increase measurement precision. If a marker is attached to a long pointer, wherein the location of the pointer tip (spaced from the marker) is of interest, a minimal angular marker location determination error translates to even greater error at the pointer's tip. Therefore, providing a tool comprising a plurality of markers will increase measurement precision. Preferably, the respective markers are positioned as far from each other as possible. Typically, three markers will be used as a compromise between ergonomics of the tool and measurement precision.

One may define a fully functional tool having a single marker as long as the measurement system comprises two cameras. Naturally, measurement precision will be decreased with respect to a tool having two or more markers.

The preferred configurations of markers on tools are such, in which markers are spaced from each other as far as possible, the tip of the tool is as close as possible to the markers and there are as many markers as possible.

The present invention provides accurate and cost effective optical tracking and measurement of distances in three-dimensional space (absolute distances and angles between points, segments and planes). Therefore, the invention provides a useful, concrete and tangible result.

The present invention is applicable in a particular machine and transforms image data into optical tracking data. Thus, the machine or transformation test is fulfilled and that the idea is not abstract.

It can be easily recognized, by one skilled in the art, that the aforementioned method for optical tracking may be performed and/or controlled by one or more computer programs. Such computer programs are typically executed by utilizing the computing resources in a computing device. Applications are stored on a non-transitory medium. An example of a non-transitory medium is a non-volatile memory, for example a flash memory while an example of a volatile memory is RAM. The computer instructions are executed by a processor. These memories are exemplary recording media for storing computer programs comprising computer-executable instructions performing all the steps of the computer-implemented method according the technical concept presented herein.

While the invention presented herein has been depicted, described, and has been defined with reference to particular preferred embodiments, such references and examples of implementation in the foregoing specification do not imply any limitation on the invention. It will, however, be evident that various modifications and changes may be made thereto without departing from the broader scope of the technical concept. The presented preferred embodiments are exemplary only, and are not exhaustive of the scope of the technical concept presented herein.

Accordingly, the scope of protection is not limited to the preferred embodiments described in the specification, but is only limited by the claims that follow.

What is claimed is:

1. A method of determining a 3D position of an object in space, the method comprising the steps of:
    attaching an optical-tracking marker to the object, said optical-tracking marker comprising an inner marker body having an elliptical shape and a geometric center, said inner marker body being filled with color spectrum points radially spread with respect to the geometric center, wherein a color value of each spectrum point of the inner marker body is calculated as a function of an angle defined between a horizontal line crossing the central point and a further line crossing the central point as well as the respective spectrum point,
    capturing a first digital image of said optical-tracking marker using a first camera and capturing a further digital image of said optical-tracking marker using a further camera,
    detecting, within the first and further digital images, edges of the optical-tracking marker,
    detecting blobs within a respective set of detected edges in the first and further digital images,
    detecting ellipses within a respective set of detected blobs,
    analyzing a sinusoidal pattern within each of the detected ellipses,
    determining, based on the analysis, a 2D location of the optical-tracking marker in each of the first digital image and the further digital image, and
    determining a 3D location of the optical-tracking marker in space based on the 2D locations in each of the first digital image and the further digital image.

2. The method of claim 1, wherein the color values of the respective spectrum points vary in accordance with the sinusoidal pattern along an elliptical path around the center point.

3. The method of claim 2, wherein the elliptical path is a circular path centered around the center point.

4. The method of claim 1, wherein the center point of the respective optical-tracking marker is estimated based on the analysis of the sinusoidal pattern within the ellipses in order to determine the 2D location of the respective optical-tracking marker.

5. The method of claim 1, wherein a number of expectations are provided, said expectations representing expected images of the optical tracking marker, and wherein the 2D position of the optical tracking marker is determined by comparing the captured digital image and the expectations.

6. The method of claim 1, wherein the respective optical-tracking marker comprises an identifier, said identifier being determined based on the analysis of the sinusoidal pattern within the ellipses.

7. The method of claim 1, wherein the respective optical-tracking marker is a grey-scale marker.

8. The method of claim 1, wherein the color values of the spectrum points each comprise three different color components.

9. The method of claim 1, wherein the inner marker body is circular.

10. The method of claim 1, wherein a radius of the inner marker body is divided into at least two sections, and wherein different color generating functions apply to different sections.

11. The method of claim 1, wherein the color value of each spectrum point is calculated according to the following equation:

$$R = C_R + A_{R1} \sin(f_{R1} \cdot \theta + \varphi_{R1}) + A_{R2} \sin(f_{R2} \cdot \theta + \varphi_{R2}) + \ldots + A_{RN} \sin(f_{RN} \cdot \theta + \varphi_{RN})$$

$$G = C_G + A_{G1} \sin(f_{G1} \cdot \theta + \varphi_{G1}) + A_{G2} \sin(f_{G2} \cdot \theta + \varphi_{G2}) + \ldots + A_{GN} \sin(f_{GN} \cdot \theta + \varphi_{RN})$$

$$B = C_B + A_{B1} \sin(f_{B1} \cdot \theta + \varphi_{B1}) + A_{B2} \sin(f_{B2} \cdot \theta + \varphi_{B2}) + \ldots + A_{BN} \sin(f_{BN} \cdot \theta + \varphi_{BN})$$

wherein

R, G, B—are color components;

C—is a fixed coefficient defining an average value of R, G, B;

A—is a value of amplitude of a geometric function such as a sine;

f—is a frequency assuming values 1, 2, 3 . . . N being a number of sinusoidal components, with $N \leq 10$ and preferably $N \leq 5$ and even more preferred $N \leq 3$);

$\theta$—is an angle defined between a horizontal line crossing the central point of the inner marker body and a line crossing the central point of the inner marker as well as the given pixel;

$\varphi$—is an initial phase—a parameter of a sine function for $\theta = 0$;

R, G, B—indexes of referenced color components.

12. The method of claim 1, wherein the optical-tracking marker further comprises an outer ring and/or a background section, which extends radially from the inner marker body.

13. The method of claim 1, wherein the object is a tool.

14. A method of determining a 3D position of an object in space, the method comprising the steps of:

attaching at least two optical-tracking markers on the object, said at least two optical-tracking markers each comprising an inner marker body having an elliptical shape and a geometric center, said inner marker body being filled with color spectrum points radially spread with respect to the geometric center, wherein a color value of each spectrum point of the inner marker body is calculated as a function of an angle defined between a horizontal line crossing the central point and a further line crossing the central point as well as the respective spectrum point, capturing a digital image of said at least two optical-tracking markers using at least one camera, detecting, within the digital image, edges of the at least two optical-tracking markers, detecting blobs within a respective set of detected edges, detecting ellipses within a respective set of detected blobs, analyzing a sinusoidal pattern within each of the detected ellipses, determining, based on the analysis, 2D locations of the at least two optical-tracking markers, and determining a 3D position of the object in space based on the 2D locations.

15. The method of claim 14, wherein the color values of the respective spectrum points vary in accordance with the sinusoidal pattern along an elliptical path around the center point.

16. The method of claim 15, wherein, wherein elliptical path is a circular path centered around the center point.

17. The method of claim 14, wherein the center point of the respective optical-tracking marker is estimated based on the analysis of the sinusoidal pattern within the ellipses in order to determine the 2D location of the respective optical-tracking marker.

18. The method of claim 14, wherein a number of expectations are provided, said expectations representing expected images of the optical tracking marker, and wherein the 2D position of the optical tracking marker is determined by comparing the captured digital image and the expectations.

19. The method of claim 14, wherein the respective optical-tracking marker comprises an identifier, said identifier being determined based on the analysis of the sinusoidal pattern within the ellipses.

20. The method of claim 14, wherein the respective optical-tracking marker is a grey-scale marker.

21. The method of claim 14, wherein the color values of the spectrum points each comprise three different color components.

22. The method of claim 14, wherein the inner marker body is circular.

23. The method of claim 14, wherein a radius of the inner marker body is divided into at least two sections, and wherein different color generating functions apply to different sections.

24. The method of claim 14, wherein the color value of each spectrum point is calculated according to the following equation:

$$R = C_R + A_{R1} \sin(f_{R1} \cdot \theta + \varphi_{R1}) + A_{R2} \sin(f_{R2} \cdot \theta + \varphi_{R2}) + \ldots + A_{RN} \sin(f_{RN} \cdot \theta + \varphi_{RN})$$

$$G = C_G + A_{G1} \sin(f_{G1} \cdot \theta + \varphi_{G1}) + A_{G2} \sin(f_{G2} \cdot \theta + \varphi_{G2}) + \ldots + A_{GN} \sin(f_{GN} \cdot \theta + \varphi_{RN})$$

$$B = C_B + A_{B1} \sin(f_{B1} \cdot \theta + \varphi_{B1}) + A_{B2} \sin(f_{B2} \cdot \theta + \varphi_{B2}) + \ldots + A_{BN} \sin(f_{BN} \cdot \theta + \varphi_{BN})$$

wherein

R, G, B—are color components;

C—is a fixed coefficient defining an average value of R, G, B;

A—is a value of amplitude of a geometric function such as a sine;

f—is a frequency assuming values 1, 2, 3 . . . N being a number of sinusoidal components, with $N \leq 10$ and preferably $N \leq 5$ and even more preferred $N \leq 3$);

$\theta$—is an angle defined between a horizontal line crossing the central point of the inner marker body and a line crossing the central point of the inner marker as well as the given pixel;

$\varphi$—is an initial phase—a parameter of a sine function for $\theta = 0$;

R, G, B—indexes of referenced color components.

25. The method of claim 14, wherein the optical-tracking marker further comprises an outer ring and/or a background section, which extends radially from the inner marker body.

26. The method of claim 14, wherein the object is a tool.

27. A system for determining a 3D position of an object in space, comprising:
- at least one optical-tracking marker configured to be attached to the object, said at least one optical-tracking marker comprising an inner marker body having an elliptical shape and a geometric center, said inner marker body being filled with color spectrum points radially spread with respect to the geometric center, wherein a color value of each spectrum point of the inner marker body is calculated as a function of an angle defined between a horizontal line crossing the central point and a further line crossing the central point as well as the respective spectrum point,
- at least one camera for capturing at least one digital image of said optical-tracking marker, and
- a processing unit configured to execute the following steps:
  - capturing a first digital image and a further digital image of said at least one optical-tracking marker, when said at least one optical-tracking marker is attached to the object, by using said at least one camera, said first digital image and said further digital image being taken from at least two different camera positions,
  - detecting, within the first and further digital images, edges of the at least one optical-tracking marker,
  - detecting blobs within a respective set of detected edges in the first and further digital images,
  - detecting ellipses within a respective set of detected blobs,
  - analyzing a sinusoidal pattern within each of the detected ellipses,
  - determining, based on the analysis, a respective 2D location of the at least one optical-tracking marker in each of the first digital image and the further digital image, and
  - determining a 3D location of the at least one optical-tracking marker in space based on the respective 2D locations in each of the first digital image and the further digital image.

28. A system for determining a 3D position of an object in space, comprising:
- at least two optical-tracking markers configured to be attached to the object, said at least two optical-tracking markers each comprising an inner marker body having an elliptical shape and a geometric center, said inner marker body being filled with color spectrum points radially spread with respect to the geometric center, wherein a color value of each spectrum point of the inner marker body is calculated as a function of an angle defined between a horizontal line crossing the central point and a further line crossing the central point as well as the respective spectrum point,
- at least one camera for capturing at least one digital image of each of said at least two optical-tracking markers, and
- a processing unit configured to execute the following steps:
  - capturing a digital image of said at least two optical-tracking markers using said at least one camera, when said at least two optical-tracking marker are attached to the object,
  - detecting, within the digital image, edges of the at least two optical-tracking markers,
  - detecting blobs within a respective set of detected edges,
  - detecting ellipses within a respective set of detected blobs,
  - analyzing sinusoidal patterns within each of the detected ellipses,
  - determining, based on the analysis, 2D locations of the at least two optical-tracking markers, and
  - determining a 3D position of the object in space based on the 2D locations.

* * * * *